United States Patent
Burattin et al.

(10) Patent No.: US 7,098,358 B2
(45) Date of Patent: Aug. 29, 2006

(54) HYDROCYANATION METHOD FOR ETHYLENICALLY UNSATURATED ORGANIC COMPOUNDS

(75) Inventors: Paolo Burattin, Lyons (FR); Jean-Christophe Galland, Lyons (FR); Alex Chamard, Corbas (FR)

(73) Assignee: Rhodia Polyamides Intermediates, Saint-Fons (FR)

( * ) Notice: Subject to any disclaimer, the term of this patent is extended or adjusted under 35 U.S.C. 154(b) by 285 days.

(21) Appl. No.: 10/399,237

(22) PCT Filed: Oct. 3, 2001

(86) PCT No.: PCT/FR01/03047

§ 371 (c)(1),
(2), (4) Date: Sep. 24, 2003

(87) PCT Pub. No.: WO02/30854

PCT Pub. Date: Apr. 18, 2002

(65) Prior Publication Data

US 2004/0063956 A1    Apr. 1, 2004

(30) Foreign Application Priority Data

Oct. 13, 2000   (FR)   ................................. 00 13152

(51) Int. Cl.
*C07C 253/00*   (2006.01)

(52) U.S. Cl. ...................................... 558/335; 558/338
(58) Field of Classification Search ................ 558/335, 558/338
See application file for complete search history.

(56) References Cited

FOREIGN PATENT DOCUMENTS

| FR | 2 588 197 | 4/1987 |
| FR | 2 785 610 | 5/2000 |
| FR | 2 785 611 | * 12/2000 |
| FR | 2785611 | * 12/2000 |
| WO | WO 00/39134 | 7/2000 |

* cited by examiner

*Primary Examiner*—Kamal A. Saeed
*Assistant Examiner*—Susannah L. Chung
(74) *Attorney, Agent, or Firm*—Buchanan Ingersoll, P.C.

(57) ABSTRACT

The invention concerns a method for hydrocyanation of ethylenically unsaturated organic compounds into compounds comprising at least a nitrile function. More particularly, it concerns a method for hydrocyanation of organic compounds comprising at least a ethylenical bond by reacting hydrogen cyanide, in the presence of a catalytic system comprising a transition metal and an organophosphorus ligand. The organophosphorus ligand is a compound with monophosphanorbornadiene structure. The invention concerns in particular hydrocyanation of butadiene into adiponitrile.

21 Claims, No Drawings

HYDROCYANATION METHOD FOR ETHYLENICALLY UNSATURATED ORGANIC COMPOUNDS

The present invention relates to a process for the hydrocyanation of organic compounds comprising ethylenic unsaturation to compounds comprising at least one nitrile functional group.

It relates more particularly to the hydrocyanation of diolefins, such as butadiene, or substituted olefins, such as alkenenitriles, for example pentenenitriles.

French Patent No. 1 599 761 discloses a process for the preparation of nitriles by addition of hydrocyanic acid to organic compounds having at least one ethylenic double bond in the presence of a nickel catalyst and a triaryl phosphite. This reaction can be carried out in the presence or absence of a solvent.

When a solvent is used in this process of the prior art, it is preferably a hydrocarbon, such as benzene or xylenes, or a nitrile, such as acetonitrile.

The catalyst employed is an organic nickel complex comprising ligands such as phosphines, arsines, stibines, phosphites, arsenites or antimonites.

The presence of a promoter for activating the catalyst, such as a boron compound or a metal salt, generally a Lewis acid, is also recommended in the said patent.

Patent FR-A-2 338 253 provided for the implementation of the hydrocyanation of compounds having at least one ethylenic unsaturation in the presence of an aqueous solution of a compound of a transition metal, in particular nickel, palladium or iron, and of a sulphonated phosphine.

The sulphonated phosphines disclosed in this patent are sulphonated triarylphosphines and more particularly sulphonated triphenylphosphines.

This process makes possible correct hydrocyanation, in particular of butadiene and pentenenitriles, and easy separation of the catalytic solution by simple separation by settling and consequently prevents as far as possible discharge of effluents or waste comprising the metals acting as catalyst.

However, research is being carried out to find novel catalytic systems which are more effective both as regards catalytic activity and as regards stability.

One of the aims of the present invention is to provide a novel family of ligands which makes it possible to obtain, with transition metals, catalytic systems exhibiting an improved activity with respect to the known systems.

To this end, the invention provides a process for the hydrocyanation of organic compounds comprising at least one ethylenic bond by reaction with hydrogen cyanide in the presence of a catalytic system comprising a transition metal and an organophosphorus ligand, characterized in that the ligand is a phosphine corresponding to the following general formula:

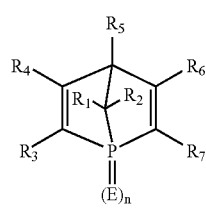

(I)

in which:

E represents O or S;

n represents 0 or 1;

$R_1$, $R_4$, $R_5$ and $R_6$, which are identical or different, represent a hydrogen atom; an optionally substituted, saturated or unsaturated, aliphatic hydrocarbonaceous radical comprising 1 to 40 carbon atoms, the hydrocarbonaceous chain of which is optionally interrupted by a heteroatom; an optionally substituted, monocyclic or polycyclic, saturated, unsaturated or aromatic, carbocyclic or heterocyclic radical; or a saturated or unsaturated, aliphatic hydrocarbonaceous radical, the hydrocarbonaceous chain of which is optionally interrupted by a heteroatom and carries a carbocyclic or heterocyclic radical as defined above, the said radical optionally being substituted;

or else $R_4$ and $R_5$ form, together with the carbon atoms which carry them, an optionally substituted, saturated or unsaturated, carbocyclic monocycle preferably having from 5 to 7 carbon atoms;

$R_2$ represents a hydrogen atom or the X radical;

$R_3$ represents the X radical or the Y radical;

it being understood that one and one alone of the $R_2$ and $R_3$ substituents represents the X radical;

X being chosen from a monocyclic or bicyclic, aromatic carbocyclic or heterocyclic radical having from 2 to 20 carbon atoms; a 1-alkenyl radical optionally exhibiting one or more additional unsaturations in the hydrocarbonaceous chain and having from 2 to 12 carbon atoms; a 1-alkynyl radical optionally exhibiting one or more additional unsaturations in the hydrocarbonaceous chain and having from 2 to 12 carbon atoms; or a —CN, $[(C_1–C_{12})$alkyl]carbonyl, $[(C_3–C_{18})$aryl]carbonyl, $[(C_1–C_{12})$alkoxy]carbonyl, $[(C_6–C_{18})$aryloxy]carbonyl, carbamoyl, $[(C_1–C_{12})$alkyl]carbamoyl or $[$di$(C_1–C_{12})$alkyl]carbamoyl radical; and Y taking any one of the meanings of $R_1$;

$R_7$ has the meaning of $R_1$, $R_4$, $R_5$ and $R_6$ or represents a hydrocarbonaceous radical comprising a carbonyl functional group or a radical of following formulae:

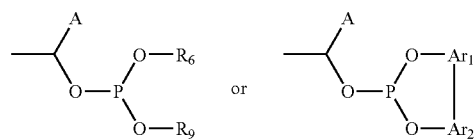

in which,

A represents a hydrogen atom; $(C_1–C_{10})$alkyl; or $(C_6–C_{10})$aryl or $(C_6–C_{10})$aryl$(C_1–C_{10})$alkyl in which the aryl part is optionally substituted by one or more radicals chosen from $(C_1–C_6)$alkyl, $(C_1–C_6)$alkoxy, trifluoromethyl, halogen, di$(C_1–C_6)$alkylamino, $(C_1–C_6)$alkoxycarbonyl, carbamoyl, $(C_1–C_6)$alkylaminocarbonyl and di$(C_1–C_6)$alkylaminocarbonyl;

—$Ar_1$—$Ar_2$— represent:

either the divalent radical of formula:

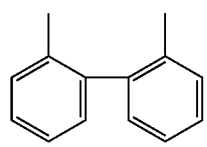

in which each of the phenyl nuclei is optionally substituted by one or more Z groups as defined below;

or the divalent radical of formula:

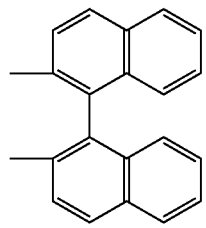

in which each of the phenyl nuclei is optionally substituted by one or more Z groups as defined below;

Z represents $(C_1-C_6)$alkyl, $(C_1-C_6)$alkoxy, trifluoromethyl, halogen, $(C_1-C_6)$alkoxycarbonyl, di$(C_1-C_6)$alkylamino, $(C_1-C_6)$alkylaminocarbonyl or di$(C_1-C_6)$alkylaminocarbonyl;

$R_8$ and $R_9$, which are identical or different, represent a substituted or unsubstituted aryl radical.

This family of phosphine compounds is disclosed in French Patent Applications Nos. 2 785 610 and 2 785 611. Examples of a process for the manufacture of these compounds are also disclosed in the abovementioned documents.

Among the compounds described, the compounds corresponding to the formula (I) in which:

$R_1$, $R_2$, $R_4$, $R_5$ and $R_6$ independently represent a hydrogen atom or else a T radical chosen from:
  a saturated or unsaturated aliphatic hydrocarbonaceous radical having from 1 to 12 carbon atoms, the hydrocarbonaceous chain of which is optionally interrupted by a heteroatom chosen from O, N and S;
  a monocyclic carbocyclic radical which is saturated or which comprises 1 or 2 unsaturations in the ring, having from 3 to 8 carbon atoms;
  a saturated or unsaturated bicyclic carbocyclic radical composed of 2 single rings condensed to one another, each single ring optionally comprising 1 to 2 unsaturations and exhibiting from 3 to 8 carbon atoms;
  a mono- or bicyclic $(C_6-C_{10})$ aromatic carbocyclic radical;
  a saturated, unsaturated or aromatic 5- to 6-membered monocyclic heterocyclic radical comprising 1 to 3 heteroatoms chosen independently from N, O and S;
  a saturated, unsaturated or aromatic bicyclic heterocyclic radical composed of two 5- to 6-membered single rings condensed to one another, each single ring comprising 1 to 3 heteroatoms chosen independently from O, N and S; and
  a saturated or unsaturated aliphatic hydrocarbonaceous radical having from 1 to 12 carbon atoms, the hydrocarbonaceous chain of which carries a carbocyclic or heterocyclic monocyclic radical as defined above, the said T radical optionally being substituted, are particularly preferred.

Preferably, X is chosen from a $(C_2-C_6)$alkenyl group, a $(C_2-C_6)$alkynyl group, phenyl, naphthyl, thienyl, furyl, pyrrolyl, imidazolyl, pyrazolyl, thiazolyl, oxazolyl, pyridyl, pyrazinyl, pyridazinyl, isothiazolyl, isoxazolyl, benzofuryl, benzothienyl, indolyl, isoindolyl, indolizinyl, indazolyl, purinyl, quinolyl, isoquinolyl, benzoxazolyl, benzothiazolyl and pteridinyl.

Among the latter, the compounds comprising a T radical optionally substituted by $(C_1-C_6)$alkyl, $(C_2-C_6)$alkenyl, $(C_1-C_6)$alkoxy or $(C_2-C_6)$acyl; a radical chosen from: $-R_a-COOR_b$, $-R_a-NO_2$, $-R_a-CN$, di$(C_1-C_6)$alkylamino, di$(C_1-C_6)$alkylamino $(C_1-C_6)$alkyl, $-R_a-CO-N(R_b)_2$, $-R_a$-hal, $-R_aCF_3$ and $-O-CF_3$ (in which $R_a$ represents a bond or $(C_1-C_6)$alkylene, $R_b$, which are identical or different, represent a hydrogen atom or $(C_1-C_6)$alkyl, and hal represents halogen);

or alternatively the radical:

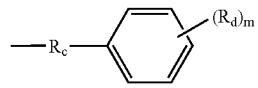

where $R_d$ is chosen from $(C_1-C_6)$alkyl, $(C_2-C_6)$alkenyl, $(C_1-C_6)$alkoxy, $(C_2-C_6)$acyl, $-R_a-COOR_b$, $-R_a-NO_2$, $-R_a-CN$, di$(C_1-C_6)$alkylamino, di$(C_1-C_6)$alkylamino $(C_1-C_6)$alkyl, $-R_a-CO-N(R_b)_2$, $-R_a$-hal, $-R_a-CF_3$ and $-O-CF_3$ (in which $R_a$, $R_b$ and hal are as defined above);

m represents an integer between 0 and 5;

$R_c$ represents a bond, $(C_1-C_6)$alkylene, $-O-$, $-CO-$, $-COO-$, $-NR_b-$, $-CO-NR_b-$, $-S-$, $-SO_2-$ or $-NR_b-O-$, $R_b$ being as defined above, are particularly preferred.

Mention may be made, as preferred compounds of the invention, of the compounds of following formulae (II) or (III):

Formula (II):

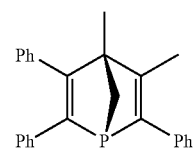

Formula (III):

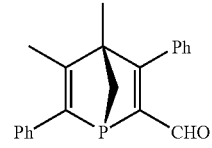

Transition metal compounds, more particularly nickel, palladium and iron compounds, are used as transition metal.

The compounds which are the most preferred among the abovementioned compounds are nickel compounds.

Mention may be made, as nonlimiting examples, of:
  compounds in which the nickel is in the zero oxidation state, such as potassium tetracyanonickelate $K_4$[Ni(CN)$_4$], bis(acrylonitrile)nickel(0), bis(1,5-cyclooctadiene)nickel and the derivatives comprising ligands from Group Va, such as tetrakis(triphenylphosphine)nickel(0), nickel compounds, such as the carboxylates (in particular the acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, arylsulphonates and alkylsulphonates.

When the nickel compound used corresponds to an oxidation state of the nickel of greater than 0, a reducing agent for the nickel is added to the reaction medium, which reducing agent preferably reacts with the nickel under the conditions of the reaction. This reducing agent can be organic or inorganic. Mention may be made, as nonlimiting examples, of $NaBH_4$, Zn powder, magnesium, $KBH_4$ and borohydrides.

When the nickel compound used corresponds to the 0 oxidation state of nickel, a reducing agent of the type of those mentioned above can also be added but this addition is not essential.

When an iron compound is used, the same reducing agents are suitable.

In the case of palladium, the reducing agents can be, in addition, components of the reaction medium (phosphine, solvent, olefin).

The organic compounds comprising at least one ethylenic double bond more particularly employed in the present process are diolefins, such as butadiene, isoprene, 1,5-hexadiene or 1,5-cyclooctadiene, aliphatic nitriles comprising ethylenic unsaturation, particularly linear pentenenitriles, such as 3-pentenenitrile or 4-pentenenitrile, monoolefins, such as styrene, methylstyrene, vinylnaphthalene, cyclohexene or methylcyclohexene, and the mixtures of several of these compounds.

The pentenenitriles in particular can comprise amounts, generally minor amounts, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, originating, for example, from the prior reaction for the hydrocyanation of butadiene to unsaturated nitriles.

This is because, during the hydrocyanation of butadiene, not insignificant amounts of 2-methyl-3-butenenitrile and 2-methyl-2-butenenitrile are formed with the linear pentenenitriles.

The catalytic system used for the hydrocyanation according to the process of the invention can be prepared before its introduction into the reaction region, for example by addition to the phosphine of formula (I), alone or dissolved in a solvent, of the appropriate amount of chosen transition metal compound and optionally of reducing agent. It is also possible to prepare the catalytic system "in situ" by simple addition of the phosphine and the transition metal compound to the hydrocyanation reaction medium, before or after the addition of the compound to be hydrocyanated.

The amount of compound of nickel or of another transition metal used is chosen in order to obtain a concentration, as mole of transition metal per mole of organic compounds to be hydrocyanated or isomerized, of between $10^{-4}$ and 1 and preferably between 0.005 and 0.5 mol of nickel or of the other transition metal employed.

The amount of phosphine of formula (I) used is chosen so that the number of moles of this compound with respect to 1 mol of transition metal is from 0.5 to 500 and preferably from 2 to 100.

Although the reaction is generally carried out without a solvent, it can be advantageous to add an inert organic solvent.

Mention may be made, as examples of such solvents, of aromatic, aliphatic or cycloaliphatic hydrocarbons.

The hydrocyanation reaction is generally carried out at a temperature of 10° C. to 200° C. and preferably of 30° C. to 120° C.

The process of the invention can be carried out continuously or batchwise.

The hydrogen cyanide employed can be prepared from metal cyanides, in particular sodium cyanide, or cyanohydrins, such as acetone cyanohydrin.

The hydrogen cyanide is introduced into the reactor in the gaseous form or in the liquid form. It can also be dissolved beforehand in an organic solvent.

In the context of a batchwise implementation, it is in practice possible to charge to a reactor, purged beforehand using an inert gas (such as nitrogen or argon), either a solution comprising all or a portion of the various constituents, such as the phosphine, the transition metal compound, the possible reducing agent and the possible solvent, or the said constituents separately. Generally, the reactor is then brought to the chosen temperature and then the compound to be hydrocyanated is introduced. The hydrogen cyanide is then itself introduced, preferably continuously and unvaryingly.

When the reaction (the progress of which can be monitored by the assaying of withdrawn samples) is complete, the reaction mixture is withdrawn after cooling and the reaction products are isolated, for example, by distillation.

An improvement to the process for the hydrocyanation of compounds comprising ethylenic unsaturation according to the present invention relates in particular to the hydrocyanation of the said nitrile compounds comprising ethylenic unsaturation by reaction with hydrogen cyanide and consists in using a catalytic system in accordance with the present invention with a cocatalyst comprising at least one Lewis acid.

The compounds comprising ethylenic unsaturation which can be employed in this improvement are generally those which were mentioned for the basic process. However, it is more particularly advantageous to apply it to the reaction for the hydrocyanation to dinitriles of aliphatic nitriles comprising ethylenic unsaturation, in particular to linear pentenenitriles, such as 3-pentenenitrile, 4-pentenenitrile and their mixtures.

These pentenenitriles can comprise amounts, generally minor amounts, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, originating from the prior reaction for the hydrocyanation of butadiene and/or from the isomerization of 2-methyl-3-butenenitrile to pentenenitriles.

The Lewis acid used as cocatalyst makes it possible in particular, in the case of the hydrocyanation of aliphatic nitriles comprising ethylenic unsaturation, to improve the linearity of the dinitriles obtained, that is to say the percentage of linear dinitrile with respect to all the dinitriles formed, and/or to increase the activity and the lifetime of the catalyst.

The term "Lewis acid" is understood to mean, in the present text, according to the usual definition, compounds which accept electron pairs.

It is possible in particular to employ the Lewis acids mentioned in the work edited by G. A. Olah, "Friedel-Crafts and Related Reactions", Volume I, pages 191 to 197 (1963).

The Lewis acids which can be employed as cocatalysts in the present process are chosen from the compounds of elements from Groups Ib, IIb, IIIa, IIIb, IVa, IVb, Va, Vb, VIb, VIIb and VIII of the Periodic Table. These compounds are generally salts, in particular halides, such as chlorides or bromides, sulphates, sulphonates, halosulphonates, perhaloalkylsulphonates, in particular fluoroalkylsulphonates or perfluoroalkylsulphonates, carboxylates and phosphates.

Mention may be made, as nonlimiting examples of such Lewis acids, of zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, the chlorides or bromides of rare-earth elements, such as lanthanum, cerium, praseodymium, neodymium, samarium, europium, gadolinium, terbium, dysprosium, holmium, erbium, thulium, ytterbium and lutetium, cobalt chloride, ferrous chloride or yttrium chloride.

It is, of course, possible to employ mixtures of Lewis acids.

Preference is very particularly given, among Lewis acids, to zinc chloride, zinc bromide, stannous chloride, stannous bromide and zinc chloride/stannous chloride mixtures.

The Lewis acid cocatalyst employed generally represents from 0.01 to 50 mol per mole of transition metal compound, more particularly of nickel compound, and preferably from 1 to 10 mol per mole.

As for the implementation of the basic process of the invention, the catalytic solution used for the hydrocyanation in the presence of Lewis acid can be prepared before its introduction into the reaction region, for example by addition, to the reaction medium of the phosphine of formula (I), of the appropriate amount of chosen transition metal compound, of the Lewis acid and optionally of the reducing agent. It is also possible to prepare the catalytic solution "in situ" by simple mixing of these various constituents.

It is also possible, under the conditions of the hydrocyanation process of the present invention and in particular by carrying out the hydrocyanation in the presence of the catalyst described above comprising at least one phosphine of formula (I) and at least one transition metal compound, to carry out, in the absence of hydrogen cyanide, isomerization of 2-methyl-3-butenenitrile to pentenenitriles and more generally of branched unsaturated nitrites to linear unsaturated nitrites.

The 2-methyl-3-butenenitrile subjected to isomerization according to the invention can be employed alone or as a mixture with other compounds.

Thus, 2-methyl-3-butenenitrile can be used as a mixture with 2-methyl-2-butenenitrile, 4-pentenenitrile, 3-pentenenitrile, 2-pentenenitrile, butadiene, adiponitrile, 2-methylglutaronitrile, 2-ethylsuccinonitrile or valeronitrile.

It is particularly advantageous to treat the reaction mixture originating from the hydrocyanation of butadiene by HCN in the presence of at least one phosphine of formula (I) and at least one compound of a transition metal, more preferably a compound of nickel in the 0 oxidation state, as defined above.

In the context of this preferred alternative form, the catalytic system being already present for the reaction for the hydrocyanation of butadiene, it is sufficient to halt any introduction of hydrogen cyanide to allow the isomerization reaction to take place.

In this alternative form, it is possible, if appropriate, to carry out a slight flushing of the reactor using an inert gas, such as nitrogen or argon, for example, in order to drive off the hydrocyanic acid which might still be present.

The isomerization reaction is generally carried out at a temperature of 10° C. to 200° C. and preferably of 60° C. to 120° C.

In the preferred case of an isomerization immediately following the reaction for the hydrocyanation of butadiene, it will be advantageous to carry out the isomerization at the temperature at which the hydrocyanation was carried out.

As for the process for the hydrocyanation of compounds comprising ethylenic unsaturation, the catalytic system used for the isomerization can be prepared before its introduction into the reaction region, for example by addition, to the reaction medium of the phosphine of formula (I), of the appropriate amount of chosen transition metal compound and optionally of the reducing agent. It is also possible to prepare the catalytic system "in situ" by simple mixing of these various constituents. The amount of transition metal compound and more particularly of nickel compound used and the amount of phosphine of formula (I) are the same as for the hydrocyanation reaction.

Although the isomerization reaction is generally carried out without a solvent, it can be advantageous to add an inert organic solvent which can be that of the subsequent extraction. This is in particular the case when such a solvent has been employed in the reaction for the hydrocyanation of butadiene which has been used to prepare the medium subjected to the isomerization reaction. Such solvents can be chosen from those which were mentioned above for the hydrocyanation.

However, the preparation of dinitrile compounds by hydrocyanation of an olefin such as butadiene can be carried out by using a catalytic system in accordance with the invention for the stages of formation of the unsaturated nitrites and the stage of isomerization above, it being possible for the reaction for the hydrocyanation of the unsaturated nitrites to dinitriles to be carried out with a catalytic system in accordance with the invention or any other catalytic system already known for this reaction.

Likewise, the reaction for the hydrocyanation of the olefin to unsaturated nitrites and the isomerization of the latter can be carried out with a catalytic system different from that of the invention, the stage of hydrocyanation of the unsaturated nitrites to dinitriles being carried out with a catalytic system in accordance with the invention.

The invention will be more clearly illustrated in the light of the examples given below by way of indication and illustration.

In these examples, the meanings of the abbreviations used are given below:

PNP:

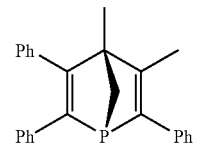

PNA:

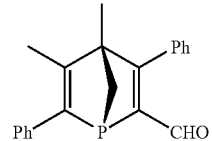

cod: 1,5-cyclooctadiene
2M3BN: 2-methyl-3-butenenitrile
2M2BN: 2-methyl-2-butenenitrile
3PN: 3-pentenenitrile 4PN: 4-pentenenitrile
ADN: adiponitrile
MGN: methyleneglutaronitrile
ESN: ethylsuccinonitrile
DN: dinitriles=ADN+MGN+ESN
AC: acetone cyanohydrin
EtPh: ethylbenzene
EG: ethylene glycol
DC (V): degree of conversion of the compound V to be hydrocyanated or isomerized, equal to the ratio of the difference between the number of moles of the compound V charged and the number of moles present at the end of the reaction to the number of moles charged
TY (U): true yield of the compound formed U=number of moles of U formed/maximum number of moles of U, calculated with respect to the number of moles of the compound V charged
YD (U): selectivity for the compound U=TY (U)/DC (V)
L: linearity=YD (ADN)/[YD (ADN)+YD (MGN)+YD (ESN)]
GC : gas chromatography
mol: mole
mmol: millimole

EXAMPLES 1 and 2

Isomerization of 2M3BN to 3PN

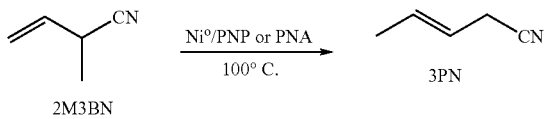

Procedure:

20 mg (0.073 mmol, M=275 g/mol, 1.0 eq) of Ni(cod)$_2$ and 5.0 eq of PNP or PNA ligand are charged to a reactor equipped with a stirrer and placed under an argon atmosphere. Approximately 1 ml (810 mg, d=0.81, M=81.12 g/mol) of degassed 2M3BN is added. The mixture is stirred and maintained at a temperature of 100° C. in a closed system for 1 hour. The reaction medium is cooled to ambient temperature (approximately 20° C.). The concentrations of the various constituents of the reaction medium are determined by analysis by GC (gas chromatography).

The results obtained and calculated from these analyses are collated in Table I below:

TABLE I

| Ex. | Ligand | Molar balance | DC (2M3BN) | YD (3 + 4PN) | YD (2M2BN) |
|---|---|---|---|---|---|
| 1 | PNP | 97% | 87% | 89% | 6% |
| 2 | PNA | 97% | 48% | 84% | 8% |

EXAMPLES 3 to 5

Hydrocyanation of 3PN to ADN

Procedure:

The ligand L (5 eq), 3PN (30 eq), Ni(cod)$_2$ (1 eq), ZnCl$_2$ (1 eq), the degassed cosolvent or cosolvents and acetone cyanohydrin (30 eq) are successively introduced at ambient temperature into a Schlenk tube maintained under argon. The mixture is brought with stirring (600 rev/min) to 65° C. for 2 hours and then brought back to ambient temperature. 3 ml of acetone are introduced to neutralize the remaining HCN. The concentrations of the various components are determined by GC analysis in order to calculate the various degrees of conversion and of selectivity.

The results obtained and calculated from these analyses are collated in Table II below:

TABLE II

| | | Charges (mmoles) | | | | Results | | |
|---|---|---|---|---|---|---|---|---|
| Ex. | Ligand L | 3PN | Ni(cod)$_2$ | ZnCl$_2$ | AC | Solvents (vol %) | DC (3PN) | YD (DN) | L (ADN) |
| 3 | PNP (2.5) | 15 | 0.44 | 0.5 | 15 | EtPh (10) | 13% | 53% | 75% |
| 4 | PNA (2.5) | 15.6 | 0.43 | 0.5 | 15.3 | | 63% | 82% | 70% |
| 5 | PNA (0.4) | 2.1 | 0.08 | 0.08 | 2.4 | EG (26) EtPh (11) | 73.2% | 65.4% | 74.4% |

EXAMPLE 6

Hydrocyanation of 3PN to ADN

Procedure:

0.506 g (6.25 mmol, M=81 g/mol) of 3PN, 340 mg (0.93 mmol, M=366 g/mol) of PNP, 1.96 g of degassed toluene, 56.5 mg (0.21 mmol, M=275 g/mol) of Ni(cod)$_2$ and 50.1 mg (0.21 mmol, M=242 g/mol) of BPh$_3$ are charged under argon to a 20 ml Schott tube equipped with a septum. The mixture is brought with stirring to 65° C. and 531 mg (6.24 mmol, M=85 g/mol) of acetone cyanohydrin are injected via the septum and using a syringe driver at a flow rate of 0.19 ml/h. After reacting for 3 h, the mixture is brought back to ambient temperature and neutralized to remove the remaining HCN. The concentrations of the various components are determined by GC analysis in order to calculate the various degrees of conversion and of selectivity.

The results obtained and calculated from these analyses are collated in Table III below:

TABLE III

| Ex. | DC (3PN) | YD (mononitriles) | YD (dinitriles) | Linearity (ADN) |
|---|---|---|---|---|
| 6 | 35% | 91.8% | 12.4% | 69% |

The Invention claimed is:

1. Process for the hydrocyanation of organic compounds comprising at least one ethylenic bond by reaction with hydrogen cyanide in the presence of a catalytic system comprising a transition metal compound and an organophosphorus ligand, wherein the ligand is a phosphine corresponding to the following general formula (I):

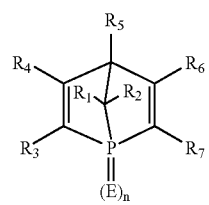

in which:
E represents O or S;
N represents 0 or 1;
$R_1$, $R_4$, $R_5$ and $R_6$, which are identical or different, represent a hydrogen atom; an optionally substituted, saturated or unsaturated, aliphatic hydrocarbonaceous radical comprising 1 to 40 carbon atoms, the hydrocarbonaceous chain of which is optionally interrupted by a heteroatom; an optionally substituted, monocyclic or polycyclic, saturated, unsaturated or aromatic, carboxyclic or heterocyclic radical; or a saturated or unsaturated, aliphatic hydrocarbonaceous radical, the hydrocarbonaceous chain of which is optionally interrupted by a heteroatom and carries a carbocyclic or heterocyclic radical as defined above, the said radical optionally being substituted;
or alternatively $R_4$ and $R_5$ form, together with the carbon atoms which carry them, an optionally substituted, saturated or unsaturated, carbocyclic monocycle;
$R_2$ represents a hydrogen atom or the X radical;
$R_3$ represents the X radical or the Y radical;
it being understood that one and one alone of the $R_2$ and $R_3$ substituents represents the X radical;
X is selected from the group consisting of a monocyclic or bicyclic, aromatic carbocyclic or heterocyclic radical having from 2 to 20 carbon atoms; a 1-alkenyl radical optionally exhibiting one or more additional unsaturations in the hydrocarbonaceous chain and having from 2 to 12 carbon atoms; a 1-alkynyl radical optionally exhibiting one or more additional unsaturations in the hydrocarbonaceous chain and having from 2 to 12 carbon atoms; or a —CN, [$C_1$–$C_{12}$alkyl]-carbonyl, [$C_3$–$C_{18}$]aryl]carbonyl, [$C_1$–$C_{12}$]alkyoxy]-carbonyl, [($C_6$–$C_{18}$)aryloxy]-carbonyl, [$C_1$–$C_{12}$]alkyl]-carbamoyl, or [di($C_1$–$C_{12}$)alkyl]carbamoyl radical; and
Y taking any one of the meanings of $R_1$, with the exception of a hydrogen atom;
$R_7$ has the meaning of $R_1$, $R_4$, $R_5$ and $R_6$ or represents a hydrocarbonaceous radical comprising a carbonyl functional group or a radical of following formulae:

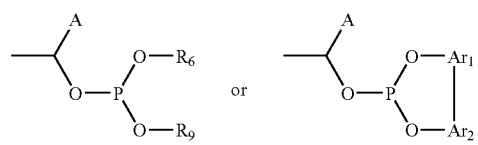

in which,
A represents a hydrogen atom; ($C_1$–$C_{10}$)alkyl; or ($C_6$–$C_{10}$)aryl or ($C_6$–$C_{10}$)aryl ($C_1$–$C_{10}$)alkyl in which the aryl part is optionally substituted by one or more radicals selected from the group consisting of ($C_1$–C6) alkyl, ($C_1$–$C_6$)alkoxy, trifluoromethyl, halogen di($C_1$–$C_6$)alkylamino, ($C_1$–$C_6$)alkoxycarbonyl, carbamoyl, ($C_1$–$C_6$)alkylaminocarbonyl and di($C_{1-C6}$) alkylaminocarbonyl;
—$Ar_1$—$Ar_2$ represents:
either the divalent radical of formula:

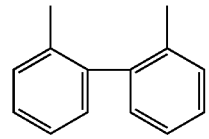

in which each of the phenyl nuclei is optionally substituted by one or more Z groups as defined below;
or the divalent radical of formula:

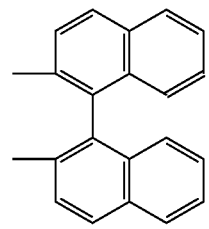

in which each of the phenyl nuclei is optionally substituted by one or more Z groups as defined below;
Z represents ($C_1$–$C_6$)alkyl, ($C_1$–$C_6$)alkoxy, trifluoromethyl, halogen, ($C_{1-C6}$) alkoxycarbonyl, di($C_1$–$C_6$) alkylamino, ($c_1$–$C_6$)alkylaminocarbonyl or di($C_1$–$C_6$) alkylaminocarbonyl;
$R_8$ and $R_9$, which are identical or different, represent a substituted or unsubstituted aryl radical.

2. Process according to claim 1, wherein the phosphine compounds are those corresponding to the formula (I) in which:

$R_1$, $R_2$, $R_4$, $R_5$ and $R_6$ independently represent a hydrogen atom or alternatively a T radical selected from the group consisting of:
- a saturated or unsaturated aliphatic hydrocarbonaceous radical having from 1 to 12 carbon atoms, the hydrocarbonaceous chain of which is optionally interrupted by a heteroatom chosen from O, N and S;
- a monocyclic carbocyclic radical which is saturated or which comprises 1 or 2 unsaturations in the ring, having from 3 to 8 carbon atoms;
- a saturated or unsaturated bicyclic carbocyclic radical composed of 2 single rings condensed to one another, each single ring optionally comprising 1 to 2 unsaturations and exhibiting from 3 to 8 carbon atoms;
- a mono- or bicyclic ($C_6$–$C_{10}$) aromatic carbocyclic radical;
- a saturated, unsaturated or aromatic 5- to 6-membered monocyclic heterocyclic radical comprising 1 to 3 heteroatoms selected independently from the group consisting of N, O and S;
- a saturated, unsaturated or aromatic bicyclic heterocyclic radical composed of two 5- to 6-membered single rings condensed to one another, each single ring comprising 1 to 3 heteroatoms selected independently from the group consisting of O, N and S; and
- a saturated or unsaturated aliphatic hydrocarbonaceous radical having from 1 to 12 carbon atoms, the hydrocarbonaceous chain of which carries a carbocyclic or heterocyclic monocyclic radical as defined above, the said T radical optionally being substituted.

3. Process according to claim 1, wherein X is selected from the group consisting of a ($C_2$–$C_6$)alkenyl group, a ($C_2$–$C_6$)alkynyl group, phenyl, naphthyl, thienyl, furyl, pyrrolyl, imidazolyl, pyrazolyl, thiazolyl, oxazolyl, pyridyl, pyrazinyl, pyridazinyl, isothiazolyl, isoxazolyl, benzoftiryl, benzothienyl, indolyl, isoindolyl, indolizinyl, indazolyl, purinyl, quinolyl, isoquinolyl, benzoxazolyl, benzothiazolyl and pteridinyl.

4. Process according to claim 1, wherein the T radical is substituted by a group selected from the group consisting of: ($C_1$–$C_6$)alkyl, ($C_2$–$C_6$)alkenyl, ($C_1$–$C_6$)alkoxy or or ($C_2$–$C_6$)acyl; a radical chosen from: —$R_a$—COOR$_b$, —$R_a$—NO$_2$, —$R_a$—CN, di($C_1$–$C_6$) alkylamino, di($C_1$–$C_6$)alkylamino($C_1$–$C_6$)alkyl, —$R_a$—CO—N($R_b$)$_2$, —$R_a$-hal, —$R_a$CF$_3$ and —O—CF$_3$ (in which $R_a$ represents a bond or ($C_1$–$C_6$)alkylene, $R_b$, which are identical or different, represent a hydrogen atom or ($C_1$–$C_6$)alkyl, and hal represents halogen);
or alternatively the radical:

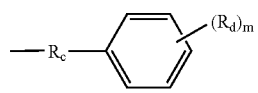

where $R_d$ is selected from the group consisting of ($C_1$–$C_6$) alkyl, ($C_2$–$C_6$)alkenyl, ($C_1$–$C_6$)alkoxy, ($C_2$–$C_6$)acyl, —$R_a$—COOR$_b$, —$R_a$—NO$_2$, —$R_a$—CN, di($C_1$–$C_6$) alkylamino, di($C_1$–$C_6$)alkylamino($C_1$–$C_6$)alkyl, —$R_a$CO—N($R_b$)$_2$, —$R_a$-hal, —$R_a$—CF$_3$ and —O—CF$_3$ (in which $R_a$, $R_b$ and hal are as defined above);

m represents an integer between 0 and 5;
$R_c$ represents a bond, ($C_1$–$C_6$)alkylene, —O—, —CO—, —COO—, —NR$_b$—, —CO—NR$_b$—, —S, —SO$_2$— or —NR$_{b—CO—}$, $R_b$ being as defined above.

5. Process according to claim 1, wherein the phosphine corresponds either to the following formula II or to the following formula III:

Formula (II):

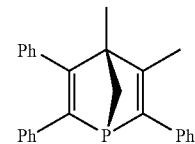

Formula (III):

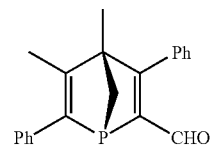

6. Process according to claim 1, wherein the transition metal compounds are selected from the group consisting of nickel, palladium and iron compounds.

7. Process according to claim 1, wherein the transition metal compound is selected from the group consisting of:
- compounds in which nickel is in the zero oxidation state, and derivatives comprising ligands from Group Va; and
- nickel compounds selected from the group consisting of nickel, carboxylates, carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, arylsulphonates and alkyl sulphonates.

8. Process according to claim 1, wherein the organic compounds comprising at least one ethylenic double bond are selected from diolefins including butadiene, isoprene, 1,5-hexadiene or 1,5-cyclooctadiene, aliphatic nitriles comprising ethylenic unsaturation, linear pentenenitriles, including 3-pentenenitrile or 4-pentenenitrile, monoclefins, including styrene, methylstyrene, vinylnaphthalene, cyclohexene or methylcyclohexene, and the mixtures of several of these compounds.

9. Process according to claim 1, wherein the amount of transition metal compound used is chosen so that there is, per mole of organic compound to be hydrocyanated, between $10^{-4}$ and 1 mol of transition metal and the amount of phosphine of formula (I) used is chosen so that the number of moles of this compound with respect to 1 mol of transition metal is from 0.5 to 500.

10. Process according to claim 1, wherein the hydrocyanation reaction is carried out at a temperature of 10° C. to 200° C.

11. Process according to claim 1 for the hydrocyanation to dinitriles of nitrile compounds comprising ethylenic unsaturation by reaction with hydrogen cyanide, wherein the reaction is carried out in the presence of a catalytic system comprising at least one compound of a transition metal, at least one phosphine of formula (I) and a cocatalyst comprising at least one Lewis acid.

12. Process according to claim 11, wherein the nitrile compounds comprising ethylenic unsaturation are selected from the group consisting of aliphatic nitriles comprising ethylenic unsaturation comprising linear pentenenitriles, 3-pentenenitrile, 4-pentenenitrile and their mixtures.

13. Process according to claim 12, wherein the linear penterienitriles comprise amounts, generally minor amounts, of other compounds, including 2-methyl-3-butenenitrile, 2-methyl-2-butenenitrile, 2-pentenenitrile, valeronitrile, adiponitrile, 2-methylglutaronitrile, 2-ethylsuccinonitrile or butadiene.

14. Process according to claim 11, wherein the Lewis acid employed as cocatalyst is selected from the group consisting of the compounds of the elements from Groups Ib, IIb, IIIa, IIIb, IVa, IVb, Va, Vb, VIb, VIIb and VIII of the Periodic Table.

15. Process according to claim 11, wherein the Lewis acid is selected from the group consisting of the salts from the group of the halides, sulphates, sulphonates, haloalkylsulphonates, perhaloalkylsulphonates, carboxylates and phosphates.

16. Process according to claim 11, wherein the Lewis acid is selected from the group consisting of zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, the chlorides or bromides of rare-earth elements, such as lanthanum, cerium, praseodymium, neodymium, samarium, europium, gadolinium, terbium, dysprosium, holmium, erbium, thulium, ytterbium and lutetium, cobalt chloride, ferrous chloride, yttrium chloride and their mixtures.

17. Process according to claim 11, wherein the Lewis acid employed represents from 0.01 to 50 mol per mol of transition metal compound.

18. Process according to claim 1, wherein butadiene is hydrocyanated and 2-methyl-3-butenenitrile present in the reaction mixture originating from the hydrocyanation of butadiene is isomerized to pentenenitriles, and the isomerization is carried out in the absence of hydrogen cyanide, and in the presence of a catalyst comprising at least one phosphine of formula (I) and at least one compound of a transition metal.

19. Process according to claim 18, wherein the 2-methyl-3-butenenitrile subjected to isomerization is employed alone or as a mixture with 2-methyl-2-butenenitrile, 4-pentenenitrile, 3-pentenenitrile, 2-pentenenitrile, butadiene, adiponitrile, 2-methylglutaronitrile, 2-ethylsuccinonitrile or valeronitrile.

20. Process according to claim 18, wherein the isomerization reaction is carried out at a temperature of 10° C. to 200° C.

21. Process according to claim 18, wherein the isomerization to pentenenitriles of 2-methyl-3-butenenitrile is carried out in the presence of at least one compound of a transition metal, of at least one phosphine of formula (I) and a cocatalyst comprising at least one Lewis acid.

* * * * *